(12) United States Patent
Lederer, IV

(10) Patent No.: US 7,327,219 B2
(45) Date of Patent: Feb. 5, 2008

(54) ENHANCED ALARM SYSTEM FOR MONITORING OF PATIENTS

(76) Inventor: Charles Henry Lederer, IV, 13109 Bramblewood La., Oak Hill, VA (US) 20171

( * ) Notice: Subject to any disclaimer, the term of this patent is extended or adjusted under 35 U.S.C. 154(b) by 184 days.

(21) Appl. No.: 10/827,332

(22) Filed: Apr. 20, 2004

(65) Prior Publication Data

US 2005/0179536 A1    Aug. 18, 2005

Related U.S. Application Data

(60) Provisional application No. 60/543,619, filed on Feb. 12, 2004.

(51) Int. Cl.
  *G08B 5/22* (2006.01)
(52) U.S. Cl. .................. 340/286.07; 340/506; 340/524; 340/525; 340/825.36; 340/825.49; 340/507; 340/693.2; 340/286.02; 340/311.2; 340/326; 340/328; 340/331; 340/332; 340/333
(58) Field of Classification Search .......... 340/286.07, 340/506, 524, 525, 531, 533, 539.12, 825.36, 340/825.49, 507, 693.2, 286.02, 311.2, 326, 340/328, 331, 332, 333
See application file for complete search history.

(56) References Cited

U.S. PATENT DOCUMENTS

| | | | |
|---|---|---|---|
| 5,319,363 A * | 6/1994 | Welch et al. .......... 340/825.36 |
| 5,534,851 A * | 7/1996 | Russek .................... 340/573.4 |
| 5,602,522 A * | 2/1997 | Pacelli ....................... 340/331 |
| 5,699,038 A * | 12/1997 | Ulrich et al. .......... 340/286.07 |
| 5,949,328 A * | 9/1999 | Latty .......................... 340/326 |
| 6,078,261 A * | 6/2000 | Davsko ................... 340/573.4 |
| 6,243,001 B1 * | 6/2001 | Kodaka ..................... 340/326 |
| 6,778,081 B2 * | 8/2004 | Matheny .................... 340/506 |
| 6,784,797 B2 * | 8/2004 | Smith et al. ............. 340/573.4 |
| 6,876,303 B2 * | 4/2005 | Reeder et al. ........... 340/573.1 |

* cited by examiner

*Primary Examiner*—Daryl C Pope
(74) *Attorney, Agent, or Firm*—Birch, Stewart, Kolasch & Birch, LLP

(57) ABSTRACT

A monitoring system for use in a building, such as a hospital provides an audible and/or visual alarm. The monitoring system includes a control unit, with a plurality of medical condition monitoring units, such as ventilators, connected thereto. A plurality of speakers and/or light sources are connected to the control unit, and are located at various different spaced-apart areas within the building. An abnormal condition, sensed at one of the plurality of medical condition monitoring units, is reported to the control unit, which in turn causes the plurality of speakers and/or light sources to issue an audible/visual alarm. An adaptor can connect a medical condition monitoring unit to the control unit. The adapter may include circuitry to render an alarm output of the medical condition monitoring unit compatible with the control unit, and to suppress an alarm output for a predetermined period of time.

7 Claims, 4 Drawing Sheets

ENHANCED ALARM SYSTEM FOR MONITORING OF PATIENTS

This application claims priority on U.S. Provisional Application No. 60/543,619 filed Feb. 12, 2004, the entire contents of which are herein fully incorporated by reference.

BACKGROUND OF THE INVENTION

1. Field of the Invention

The present invention relates to a monitoring system which enhances or supplements established monitoring systems in hospitals and nursing home type environments. More particularly, the present invention concerns a monitoring system for a plurality of medical conditioning monitoring units, such as ventilators.

2. Description of the Background Art

In hospital and nursing homes, patients are often connected to medical condition monitoring equipment, such as ventilators. These ventilators have self-diagnostic sensors to determine if the ventilator (or other type of device) is properly functioning. Further, the ventilator can include sensors to determine if the patient is responding properly (e.g., breathing, normal heart beat rate, blood pressure, temperature, etc.).

If an abnormal occurrence is sensed, the ventilator or other type of monitoring device raises an alarm. The alarm can be raised by an audible sound or blinking light on the monitoring device itself, and/or above the door of the patient's room, and/or on an annunciator panel at a nurses' desk.

There are drawbacks associated with the background art discussed above.

SUMMARY OF THE INVENTION

It is an object of the present invention to address one or more of the drawbacks associated with the background art devices.

First, a nurse on duty is sometimes not at the nurse's desk or in the vicinity of the patient's room. Therefore, an alarm is not heard or seen immediately, and hence the nurse is delayed in responding to the situation. According to an article published by the Joint Commission on Accreditation of Healthcare Organizations, entitled Sentinel Event ALERT, Issue 25, Feb. 26, 2002, a study concluded on Jan. 22, 2002 reviewed nineteen deaths and four comas, which resulted in patients using ventilators. The study cited that the alarming ventilator not being audible in all areas was a contributing factor in twenty-two percent of the deaths and commas.

It is an object of the present invention to make alarms audible in the entire work area of the nurses. In other words, the alarm will be raised at many point sources in the working area (floor, wing, ICU section, maternity ward, etc.) that is relevant to the nurse's tasks.

Second, once triggered, the common annunciator panel continues to announce an alarm condition until the nurse resets the monitoring equipment attached to the patient. Since, an alarm triggering event can be raised by a minor occurrence, such as the patient coughing into the ventilator, the annunciator panel is constantly alarming. This reduces the nurse's attentiveness to alarms, since most are not serious. Therefore, it is an object of the present invention to provide an alarming system which alarms during only a continuing period of unusual occurrence at the monitoring device. In other words, the alarming unit would briefly alarm if the patient coughs into the ventilator, but would not continue to alarm until the ventilator is reset.

Third, alarms which are localized at the monitoring unit, at the door of the patient's room, or at the nurse's desk are usually set at a high volume so that they can be heard at some distance away from the source. This is required because often the nurse is distanced from the source while performing other tasks, such as cleaning, or caring for another patient. However, when the nurse is next to an alarming source, the sound is startling and annoying in its high volume level. It is an object of the present invention to provide an alarming system which is not startling, such as an alarming system which has a uniform comfortable volume, or a visual effect which is visible, throughout the working area of the nurse (nurse's desk, patients' rooms, bathroom, break room, storage closets, hallways, etc.).

Fourth, many hospitals, insurance companies and/or associations are recommending or requiring that a back-up alarming system be provided. In other words, when an alarm is raised in accordance with the conventional systems, an additional or supplemental alarm should also be raised. Further, the supplemental alarm should be duplicative, so that failure of the first alarm does not dictate a failure in the supplemental alarm. It is an object of the present invention to provide an alarm system which supplements existing alarm systems, currently employed at medical facilities, and hence is considered a back-up alarming system.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limits of the present invention, and wherein.

DETAIL DESCRIPTION OF PREFERRED EMBODIMENTS

Figure 1:
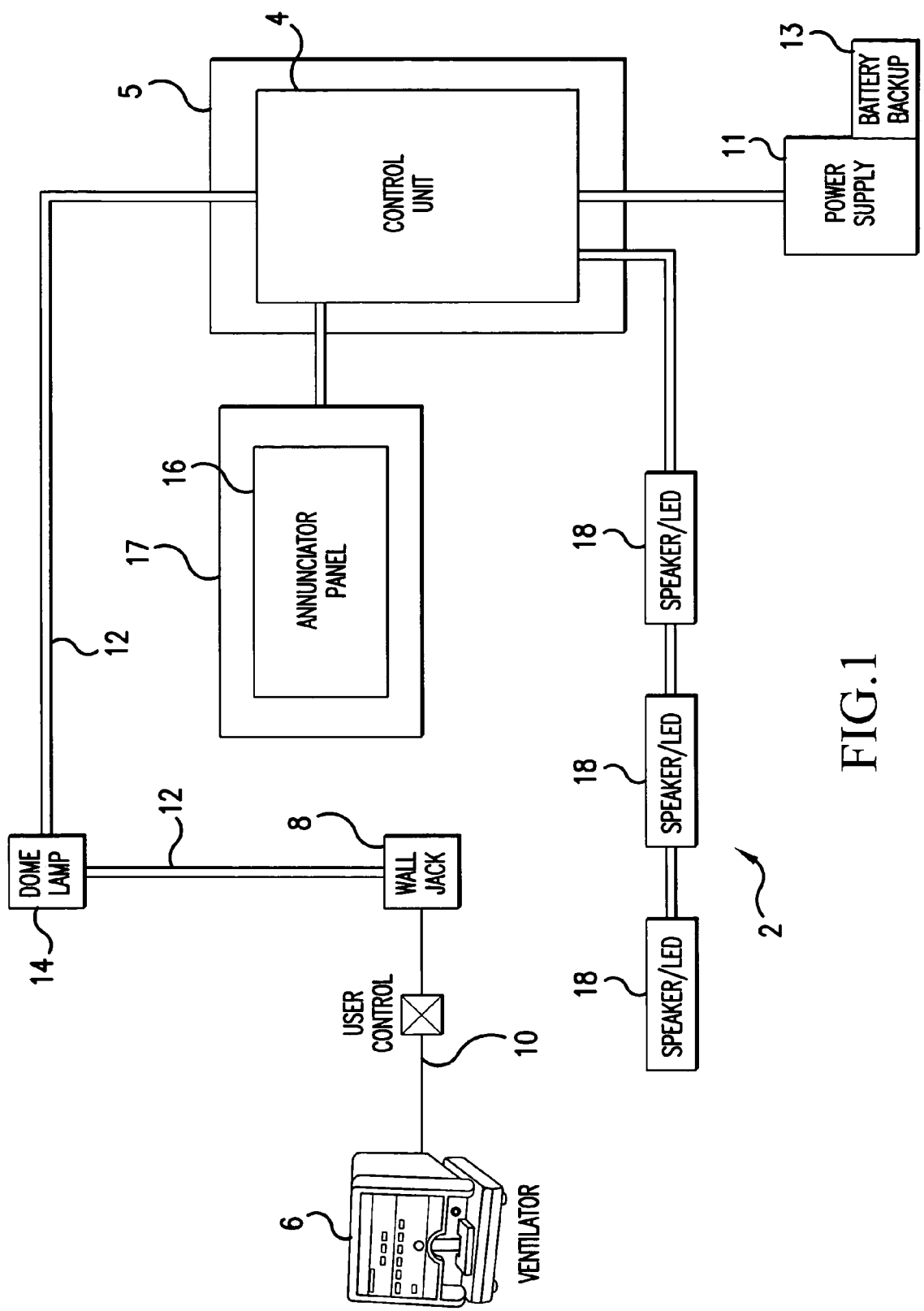
FIG. 1 is a block diagram illustrating a monitoring system, in accordance with the present invention.

FIG. 1 illustrates a system 2 for monitoring the medical conditions of one or more patients in a building, such as a hospital or nursing home. The system 2 includes a control unit 4, which would be placed in a secure area, such as a service closet 5 inside of the hospital. Several medical condition monitoring units, such as ventilators 6, are connected to the control unit 4 (FIG. 1 illustrates only one medical condition monitoring unit, or ventilator 6, connected to the control unit 4 in order to simplify the illustration).

The ventilator 6 is first connected to a wall jack 8 by an interface cable 10. The wall jack 8 is then either directly connected to the control unit 4 by a cable 12, or alternatively is connected to the control unit 4 after the cable 12 passes thorough a dome lamp 14. The dome lamp 14 would be located proximate a patient room's doorway 15, to provide a visual indication of the patient's room which needs attention because of an abnormal condition sensed by the ventilator 6.

The control unit 4 is connected to an annunciator panel 16. The annunciator's panel 16 would be located at a nurse's station 17, or some other centralized control area of the hospital. The annunciator panel 16 could be any type of known annunciator panel, such as the Series A-4060 manufactured by Cornell Communications, Inc.

Whenever, an alarm condition is sensed by the ventilator 6, the ventilator sends an alarm signal over the interface cable 10, through the cable 12 to the control unit 4. The control unit 4 passes the alarm signal along to the annunciator panel 16. The alarm signal causes audible and/or visual alarms to be displayed on the annunciator panel 16, to alert any nurse or attendant located at the nurse's station 17.

However, in accordance with the present invention, the control unit 4 also controls a plurality of spaced apart point alarm sources 18. The point alarm sources 18 may take the form or speakers, light sources (such as high output LEDs), and preferably a combination of both. The point alarm sources 18 may be mounted in the ceilings or walls in and around the work area relevant to a nurse or attendant of a particular wing or ward of a hospital.

The point alarm sources 18 are located at various different spaced-apart areas within the hospital. Whenever, the control unit 4 receives an alarm signal from a medical condition monitoring unit (e.g. ventilator 6), the control unit causes the point alarm sources 18 to issue an audible and/or visual alarm.

Figure 2:
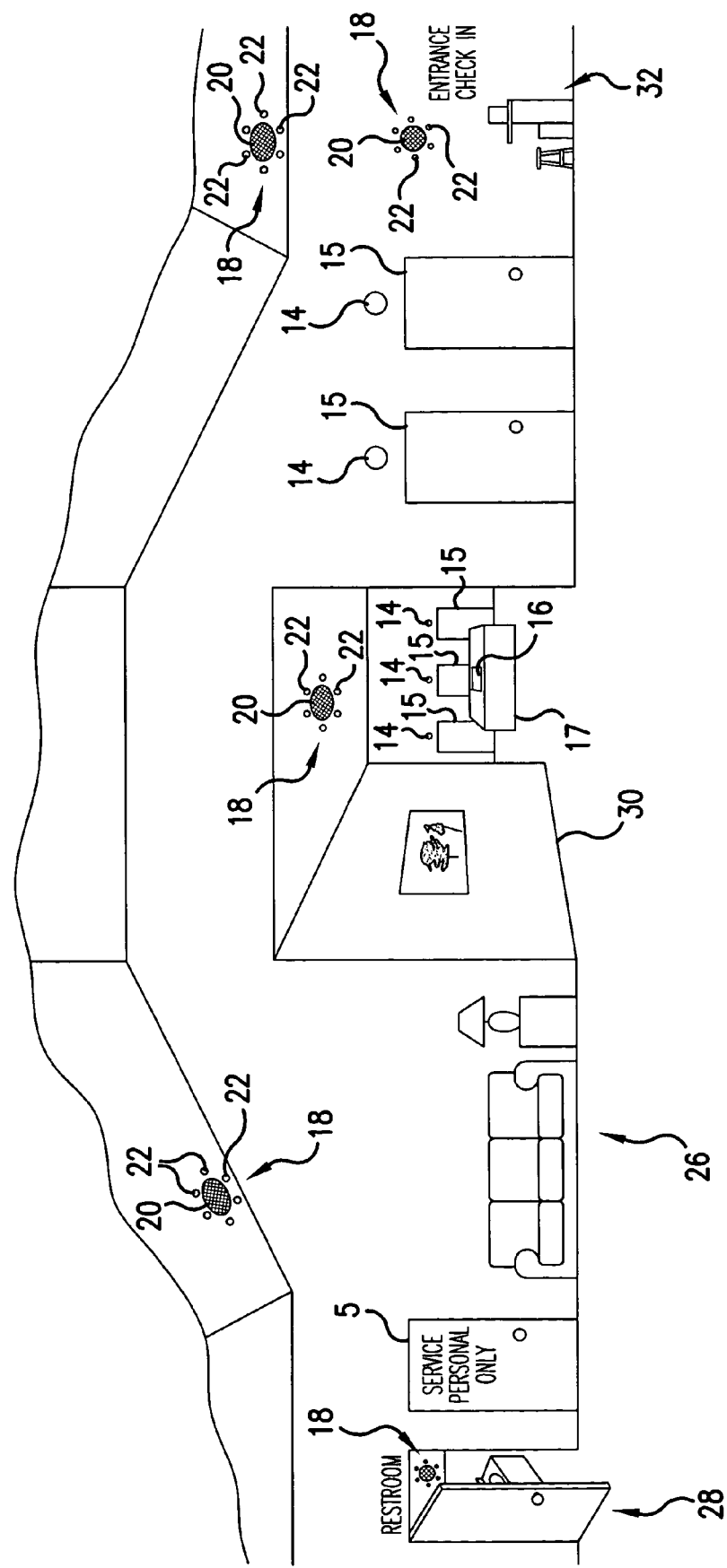
FIG. 2 is a perspective view of a section of a hospital wing, employing the monitoring system of FIG. 1.

As illustrated in FIG. 2, the point alarm sources may include a speaker 20 and one or more light sources, such as high output LEDs 22. If an alarm signal is received at the control unit 4, the control unit 4 will cause the speakers 20 to emit an audible alarm, such as a constant or pulsing tone. The audible alarm need not be an annoying sound, nor does it need to have a startling volume. Rather, the audible alarm can have a moderate volume and a distinctive chime, melody or rhythm.

The speakers 18 are placed at various locations throughout the work area of the nurse or attendant, such as a waiting room 26, restroom 28, hallway 30, entrance area 32, etc. By having the speakers 20 placed at spaced apart areas, the volume of any one speaker does not need to be adjusted to a high volume, so as to be startling to a person in the immediate proximity of the speaker 20. For example, an attendant in the restroom 28 would be able to hear the speaker 20 located in the restroom, and would not need to rely on hearing an alarm being announced at the annunciator panel 16 at the nurse's desk 17.

In a hospital environment, there are many noises to contend with. There are medical staff, police, and rescue workers, who are receiving radio dispatches, cellular phone calls, pages, etc. Moreover, many patients and visitors also have ringing cellular phones and beeping pagers. The present invention provides the hospital staff the opportunity to select a tone, chime, or rhythm that is distinct, and can be readily recognized. Further, the tone, chime or rhythm can be changed by the hospital staff at a later date, if desired. Moreover, the volume of individual speakers 20 can be independently adjusted so that a substantially constant volume for the audible alarm can be achieved throughout the work area of the nurse or attendant. For example, the volume of one speaker 20 can be set louder than the other speakers 20, such that a speaker 20 at the entrance 32 might be louder than the speaker 20 in the restroom 28.

In a preferred embodiment, the volume output by the speakers 20 in response to a single alarm event would increase over time. In other words, the audible alarm would grow in intensity or volume, until a nurse or attendant responded to the alarm, such as by pushing a reset button located on a ventilator 6 once the attendant reaches the patient.

Alternatively, the pitch or tone of the audible alarm could change to a more annoying pitch or tone. For example, the tone could increase or begin to intermediately pulse at a higher and higher frequency, until the nurse or attendant responds to the alarm. Of course, the tone or pitch change could be employed in combination with the volume increase.

As illustrated in FIG. 2, the point alarm sources 18 could also include the light sources, such as LEDs 22. FIG. 2 illustrates the LEDs 22 as surrounding the speakers 20. However, the LEDs 22 could also be located on or inside the grills of the speakers 20, or even spaced from the speakers 20.

Like the speakers 20, the LEDs 22 provide an alarm which can alert a nurse or attendant throughout the work area of the relevant wing or ward of the hospital. The LEDs 22 provide a visual alarm, such as by brightly flashing. In the noisy environment of a hospital, often a flashing alarm will be noticed prior to an audible alarm. Similar to the situation with the speakers 20, the intensity of the flash and/or the frequency of the flashing can be increased unit the alarm is answered by the nurse or attendant.

As illustrated in FIG. 1, the control unit 4 is connected to a power supply 11. The power supply 11 is typically an AC power supply. The AC power may be converted into a DC voltage by a transformer before being transmitted to the control panel 4, or within the control panel 4, so as to power integrated circuits within the control unit 4.

FIG. 1 illustrates a battery backup 13 connected to the power supply 11. The battery backup 13 could alternatively be separated from the power supply 11, e.g. be provided inside or adjacent to the control unit 4. The battery backup 13 powers the control unit 4 in the event of a power failure, and therefore it is important to monitor a status of the charge of the battery backup 13.

The control unit 4 monitors the charge status of the battery backup 13. If the charge is low, which might indicate a dead cell in the battery backup 13, the control unit 4 outputs an audible and/or visual alarm, via the speakers 20 and/or LEDs 22. The audible or visual alarm may be distinct from the alarm indicating an abnormality at a medical condition monitoring device, such as a ventilator 6. For example, the alarm could be of a different sound, or the LEDs could flash at a different frequency or pattern.

In most installations, the interface cable 10 of FIG. 1 could simply connect alarm output terminals of the medical condition monitoring unit to the wall jack 8. In such circumstances, the alarm output terminals would show one of two states to the interface cable 10. For example, in a first state (considered a normal condition state) the alarm output terminals show an open circuit to the interface cable 10. In a second state (an alarm condition state), the alarm output terminals show a short circuit to the interface cable 10.

The control unit 4 is set up to know the two states of the particular medical condition monitoring unit. In other words, the control unit 4 is established or programmed to know that an open circuit for that particular medical condition monitoring unit means normal patient conditions, whereas a short circuit means an abnormal patient condition.

Of course, the reverse conditional states could be possible for certain medical condition monitoring units. In other words, the open circuit could indicate an abnormal patient condition, while the short circuit indicates a normal patient condition. Again, the control unit 4 would be programmed to respond as appropriate for each medical condition monitoring unit.

Some medical condition monitoring units are more complex in their alarm outputs. For example, the Siemens brand "Servo 330"™ ventilator outputs a 5 volt signal during normal operating conditions and outputs a 0 volt signal during an alarm condition.

Figure 3:
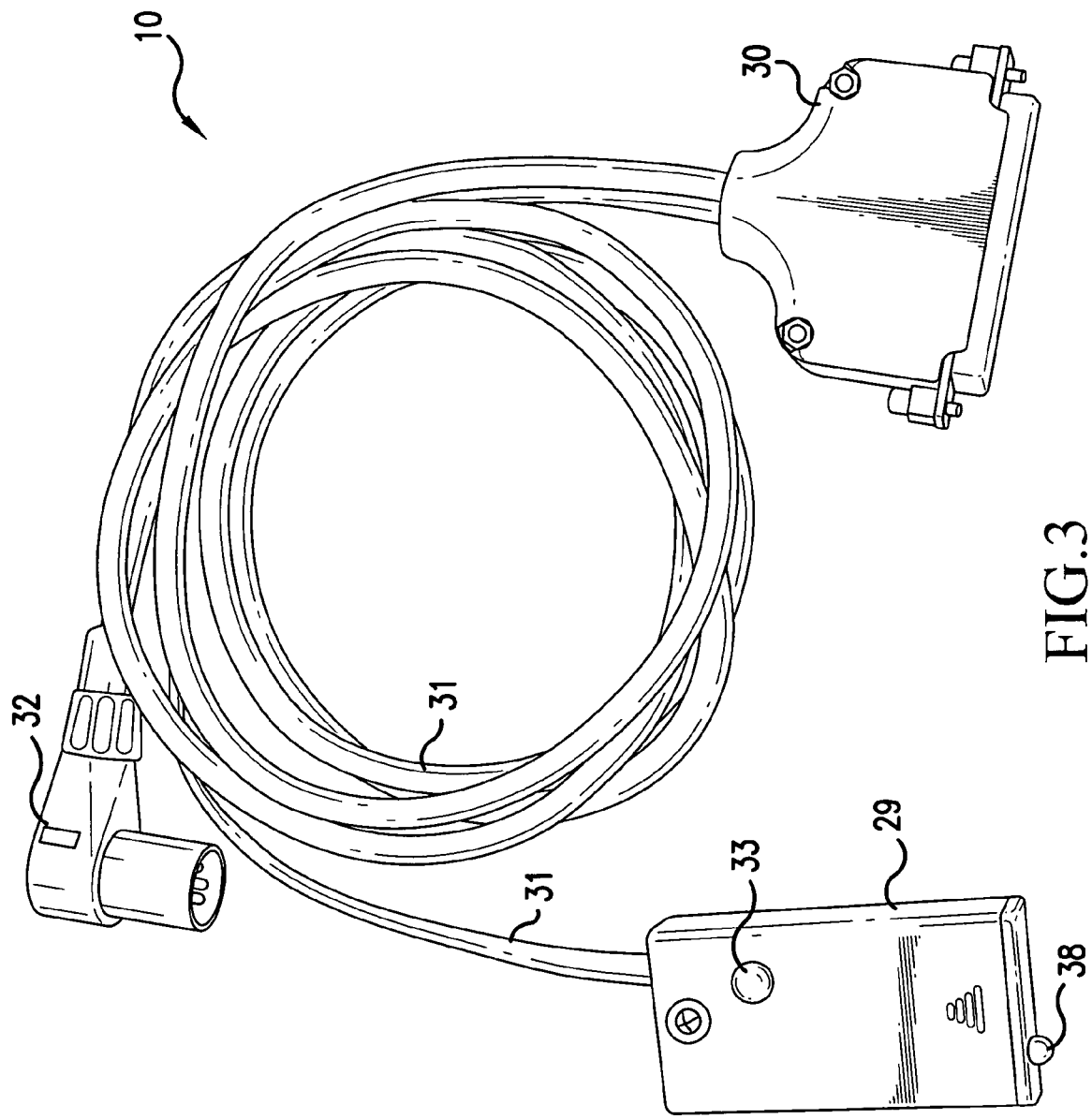
FIG. 3 is perspective view of an interface cable, illustrated in FIG. 1.

FIG. 3 is a perspective view illustrating an interface cable 10 which can accommodate a medical condition monitoring unit having a 0/+5 volt alarm output. The interface cable 10 of FIG. 3 is able to convert the 0/+5 volt alarm output into an open circuit/short circuit type of alarm output which is compatible with the control unit 4. Moreover, the interface cable 10 of FIG. 3 includes an alarm signal suppression circuit which can be used to suppress an alarm condition on a medical condition monitoring unit, regardless of the whether it uses the 0/+5 volt output conditions or the open/short circuit conditions.

In FIG. 3, the interface cable 10 includes a circuitry box 29, wiring 31, a first plug 30 and a second plug 32. The first plug 30 is a multi-pin plug and is adapted to connect to an output jack on a ventilator, such as the Siemens brand "Servo 330"™ ventilator. The second plug 32 is adapted to connect to the wall jack 8. The circuit box 29 has a user actuated switch 33, such as a momentary switch, and a light, such as an LED 38, provided thereon.

Figure 4:
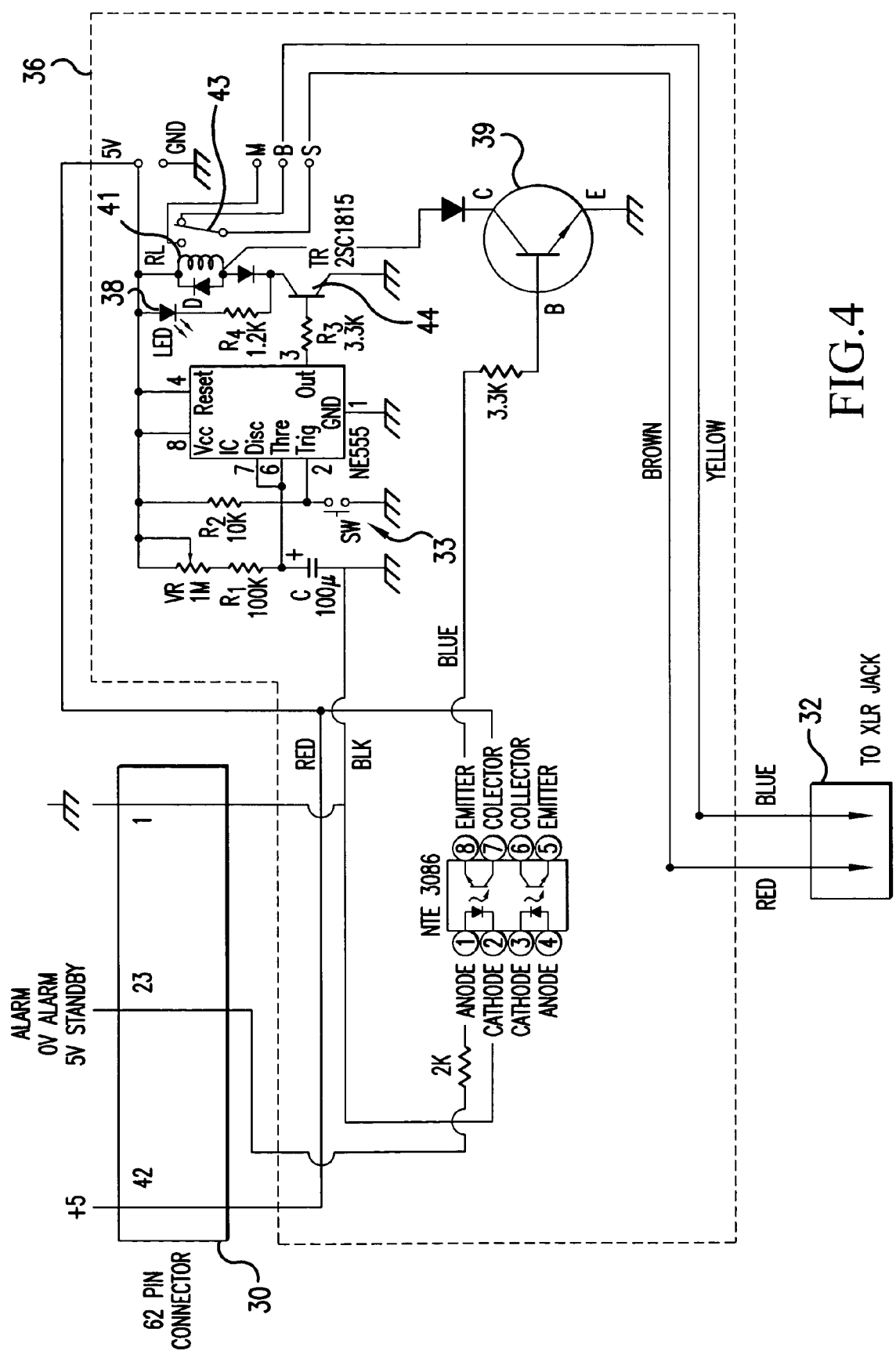
FIG. 4 is a circuit diagram for a time delay feature of the interface cable of FIG. 2.

FIG. 4 is a circuit diagram illustrating the components and interconnections of the interface cable 10 of FIG. 3. As illustrated in FIG. 4, the first plug 30 electrically connects to pins 1, 23, and 42 of the Siemens ventilator 6. Pins 1 and 42 are ground and +5 volts, respectively. Pin 23 is the alarm signal output for the ventilator 6. A voltage of +5 volts at pin 23 represents a normal patient condition, as sensed by the ventilator 6. Whereas, a voltage of 0 volts at pin 23 indicates an abnormal patient condition, as sensed by the ventilator 6. An abnormal condition sensed by the ventilator 6 could indicate that the patient has stopped breathing, is breathing erratically, is coughing, is choking, etc.

When the output at pin 23 is 5 volts (normal patient condition) the transistor 39 is turned on. This allows current to flow through solenoid coil 41. When the solenoid coil 41 is powered, the solenoid switch 43 shows an open circuit to two contacts within the second plug 32. Thus, the interface cable 10 has converted a +5 volt input at the first plug 30 into an open circuit condition at the second plug 32.

When the output at pin 23 is 0 volts (abnormal patient condition) the transistor 39 is turned off. Therefore, the transistor 39 does not provide a current flow path for the solenoid coil 41. When the solenoid coil 41 is not powered, the solenoid switch 43 shows a short or closed circuit to the two contacts within the second plug 32 (this is the condition illustrated in FIG. 4). Thus, the interface cable has converted a 0 volt alarm input at to the first plug 30 into an short circuit condition at the second plug 32.

The interface cable 10 of FIG. 4 also provides a suppression function for the alarm output signal. If the user actuated switch 33 is pressed, the LED 38 is illuminated. More importantly, the solenoid coil 41 is provided with an alternate path to ground, via transistor 44. The transistor 44 is turned on to allow the solenoid coil 41 to be energized for a predetermined period of time. Therefore, the two contacts within the second plug 32 will show an open circuit for the predetermined period of time, regardless of the voltage at pin 23 at the first plug 30.

The predetermined period of time could be approximately two minutes. The suppression of the alarm could be very beneficial to nurses and attendants. For example, often a nurse will clean or adjust a ventilator connected to a patient. These actions will cause an abnormal condition to be sensed and the alarm output to occur. However, in this circumstance, the nurse is present with the patient. Therefore, there is no need to report the alarm to the control unit 4.

The suppression circuit greatly reduces the number of alarms caused by nurses working with medical condition monitoring units connected to patients. This makes the work environment more peaceful. Further, this advantage increases the noticeability of any one alarm by reducing the number of false alarms, or alarms which do not need the notice of others.

Whenever the suppression circuit is activated, the LED 38 will illuminate. Therefore, the nurse will know when it is OK to adjust or clean the medical device's connections to the patient.

Although one type of circuit has been illustrated in FIG. 4, it should be appreciated that other types of circuits could be substituted to perform the same functions. It is the intent of the appended claims to capture the illustrated circuit and equivalents thereto, which perform the same function, as claimed.

Although the attached description focuses on ventilators, it should be noted that the system may be employed in conjunction with other medical condition monitoring devices, such as blood pressure monitors, heart beat rate monitors, temperature monitors, brainwave monitors, life support/organ function substitution devices, etc.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

I claim:

1. A system for monitoring medical conditions of one or more patients in a building, said system comprising:
   a control unit;
   a plurality of medical condition monitoring units connected to said control unit; and
   a plurality of speakers connected to said control unit, with said speakers being located at various different spaced-apart areas within the building, wherein an abnormal condition sensed at one of said plurality of medical condition monitoring units is reported to said control unit, and said control unit causes said plurality of speakers to issue an audible alarm;
   wherein said control unit has a battery backup, and wherein said control unit causes said plurality of speakers to issue the audible alarm at a first tone and/or volume in response to an abnormal condition sensed at one of said medical condition monitoring units, and causes said plurality of speakers to issue the audible alarm at a second and different tone and/or volume in response to a low battery backup condition.

2. A system for monitoring medical conditions of one or more patients in a building, said system comprising:
   a control unit;

a plurality of medical condition monitoring units connected to said control unit; and a plurality of light sources connected to said control unit, with said light sources being located at various different spaced-apart areas within the building, wherein an abnormal condition sensed at one of said plurality of medical condition monitoring units is reported to said control unit, and said control unit causes said plurality of light sources to emit light, so as to issue a visual alarm;

wherein said light sources blink with a certain frequency, and wherein said certain frequency increases over time, as the visual alarm continues.

3. The system of claim 2, wherein said plurality of light sources are located in the ceiling and/or walls of the building.

4. The system of claim 2, wherein said plurality of medical condition monitoring units are ventilators, and are hardwired to said control unit.

5. A system for monitoring medical conditions of one or more patients in a building, said system comprising:

a control unit;

a plurality of medical condition monitoring units connected to said control unit; and a plurality of light sources connected to said control unit, with said light sources being located at various different spaced-apart areas within the building, wherein an abnormal condition sensed at one of said plurality of medical condition monitoring units is reported to said control unit, and said control unit causes said plurality of light sources to emit light, so as to issue a visual alarm;

wherein said light sources emit light at a certain intensity, and wherein said light intensity increases over time, as the visual alarm continues.

6. The system of claim 5, wherein said light sources blink with a certain frequency, and wherein said certain frequency increases over time, as the visual alarm continues.

7. A system for monitoring medical conditions of one or more patients in a building, said system comprising:

a control unit;

a plurality of medical condition monitoring units connected to said control unit;

a plurality of speakers connected to said control unit, with said speakers being located at various different spaced-apart areas within the building, wherein an abnormal condition sensed at one of said plurality of medical condition monitoring units is reported to said control unit, and said control unit causes said plurality of speakers to issue an audible alarm;

a plurality of light sources connected to said control unit, with said light sources being located at various different spaced-apart areas within the building, wherein said control unit causes said plurality of light sources to emit light, so as to issue a visual alarm, whenever an abnormal condition is sensed at one of said plurality of medical condition monitoring units; and an adaptor connecting one of said plurality of medical condition monitoring units to said control unit of said monitoring system, said adapter including:

an input terminal for connection to an alarm output of one of said plurality of medical condition monitoring units;

an output terminal for connection to said control unit; and circuitry including a switch, wherein in a first switch position, an alarm condition present at said alarm output of said one of said plurality of medical condition monitoring units is substantially immediately passed to said output terminal, and wherein in a second switch position, an alarm condition present at said alarm output of said one of said plurality of medical condition monitoring units is suppressed.

* * * * *